(12) United States Patent
Tang et al.

(10) Patent No.: US 11,567,057 B2
(45) Date of Patent: Jan. 31, 2023

(54) LANDSLIDE EXPERIMENTAL DEVICE FOR SIMULATING CONSTANT SEEPAGE FLOW

(71) Applicants: Huiming Tang, Hubei (CN); Kun Fang, Hubei (CN); Yaofei Jiang, Hubei (CN); Yi Zhang, Hubei (CN); Jin Wu, Hubei (CN); Qiangqiang Jiang, Hubei (CN); Qinwen Tan, Hubei (CN)

(72) Inventors: Huiming Tang, Hubei (CN); Kun Fang, Hubei (CN); Yaofei Jiang, Hubei (CN); Yi Zhang, Hubei (CN); Jin Wu, Hubei (CN); Qiangqiang Jiang, Hubei (CN); Qinwen Tan, Hubei (CN)

(73) Assignee: Kun Fang, Wuhan (CN)

( * ) Notice: Subject to any disclaimer, the term of this patent is extended or adjusted under 35 U.S.C. 154(b) by 1102 days.

(21) Appl. No.: 16/200,603

(22) Filed: Nov. 26, 2018

(65) Prior Publication Data
US 2019/0113496 A1    Apr. 18, 2019

(51) Int. Cl.
*G01N 33/24*     (2006.01)
*E03C 1/05*     (2006.01)
(Continued)

(52) U.S. Cl.
CPC ............. *G01N 33/246* (2013.01); *E01C 1/00* (2013.01); *E02B 1/02* (2013.01); *G09B 23/40* (2013.01); *E03C 1/055* (2013.01); *G01N 2203/0003* (2013.01); *G01N 2203/0048* (2013.01); *G01N 2203/0062* (2013.01);
(Continued)

(58) Field of Classification Search
CPC ......... G01N 33/246; G01N 2203/0003; G01N 2203/0048; G01N 2203/0062; G01N 2203/0071; G01N 2203/0092; G01N 2203/0218; G01N 2203/0242; G01N 15/08; G01N 3/567; G01N 13/00; G01N 3/02; G01N 19/02; G01N 24/081; G01N 5/02; G01N 9/24; G01N 29/04; G01N 25/12; E01C 1/00; E02B 1/02; G09B 23/40; G09B 25/00; G09B 23/12; E03C 1/055; G01F 23/00; E21B 43/20
See application file for complete search history.

(56) References Cited

U.S. PATENT DOCUMENTS 3,988,243 A * 10/1976 Huff .................. B01D 35/20
                                              209/269
9,905,137 B2 * 2/2018 Jeong ................... G09B 23/12
(Continued)

*Primary Examiner* — Brandi N Hopkins

(57) ABSTRACT

The present invention discloses a landslide experimental device for remotely controlling and simulating a constant seepage flow and weight load and an experimental method thereof in centrifuge test. The landslide experimental device includes a model box, a landslide device, a near-constant water flow control box, remote control devices and a water outlet pipe. The landslide device comprises a landslide model, a load balancing device, a weight storage device, an angle control panel and a tension bar. The remote control devices are arranged at the control box water outlet, at the control box water inlet, on the tension bar, on telescoping control sensors and on the weight storage device, respectively. With the present invention, the influences on the stability of landslide model with different landslide angles under the condition of the seepage flow and weight load can be simulated.

6 Claims, 4 Drawing Sheets

(51) Int. Cl.
*G09B 23/40* (2006.01)
*E02B 1/02* (2006.01)
*E01C 1/00* (2006.01)

(52) U.S. Cl.
CPC ............... *G01N 2203/0071* (2013.01); *G01N 2203/0092* (2013.01); *G01N 2203/0218* (2013.01); *G01N 2203/0242* (2013.01)

(56) References Cited

U.S. PATENT DOCUMENTS

| | | | |
|---|---|---|---|
| 11,391,181 B2* | 7/2022 | O'Donnell | H02M 1/0003 |
| 2013/0263681 A1* | 10/2013 | Jeong | G09B 23/12 |
| | | | 73/865.6 |
| 2016/0047724 A1* | 2/2016 | Jeong | G01N 3/24 |
| | | | 73/784 |

* cited by examiner

LANDSLIDE EXPERIMENTAL DEVICE FOR SIMULATING CONSTANT SEEPAGE FLOW

BACKGROUND OF THE INVENTION

The present invention relates to the technical field of landslide experiments, and in particular to a landslide experimental device for remotely controlling and simulating a constant seepage flow and weight load and an experimental method thereof.

With the deterioration of natural conditions and the frequent occurrence of natural disasters such as earthquakes, landslides and debris flows, some scholars have done a lot of researches on the failure mechanism and migration process of landslides in recent years. China, Japan and other counties are the countries with frequent occurrence of geological disasters such as landslides, collapses and debris flows, among which the occurrence of landslides is often sudden, of high-frequency and destructive. Landslides are generally recognized as the second natural disaster ranking below earthquakes and one of the most widespread, most destructive and longest geological disasters facing humanity. The landslide stability has always been the most basic but most important research topic in the field of landslide disaster, and scientific and reasonable evaluation of the landslide stability is of great significance to ensure people's life and property safety and ensure the normal operation of the project. The formation and occurrence of landslides caused by rainfall, flash floods, earthquakes and other factors is a very complicated natural phenomenon, and it is very difficult to describe it by mathematical models. At present, many researchers are trying to explore the formation mechanism of landslides by using experiments, among which the physical model test of landslides is one of the effective means to study the failure mechanism of landslides.

Among many factors affecting the landslide stability, water is a crucial external factor. A large number of facts show that over 90% of landslide instability is closely related to water. Therefore, it is of great significance to study the stability at different landslide angles under the condition of the seepage flow and surcharge.

As a test technology aiming at the specific research object of landslides in the geo-mechanical model tests, the landslide model test has developed through the stages of frame model test, bottom friction model test, on-site 3D and full-scale model test, seepage force model test, soil and water centrifugal model test, etc. At present, most of the commonly used geo-mechanical model tests are frame model test and centrifugal model test.

In the existing centrifugal model test, the models are mostly landslide models with a fixed angle. When it is necessary to change the landslide angle, manual mounting and disassembly of the model are required, which is not only time-consuming and laborious, but also will cause a large amount of material waste and increase the cost.

BRIEF SUMMARY OF THE INVENTION

To solve the problems, the present invention provides a landslide experimental device for remotely controlling and simulating a constant seepage flow and weight load and an experimental method thereof. The structure is simple, and both the assembly and disassembly are time-saving and labor-saving.

To achieve the objective, the technical solution of the present invention is to provide a landslide experimental device for simulating a constant seepage flow, which includes a model box, a landslide device, a near-constant water flow control box, a water outlet pipe and several remote control devices; the landslide device is mounted within the model box, the near-constant water flow control box is fixedly mounted on the top of the model box, and a control box water outlet and a control box water inlet are formed on the near-constant water flow control box; an anti-overflow device is disposed at an upper end of an inner wall of the near-constant water flow control box, and two telescoping control sensors are mounted on an inner bottom of the near-constant water flow control box; each of the telescoping control sensors includes a water sensor probe and a telescopic device which can lengthen and shorten; the landslide device includes a landslide model, a load balancing device, a weight storage device, an angle control panel and a tension bar; support chutes are provided on two sides of the top of the angle control panel, and a fixed member is provided on the bottom of the angle control panel; a tension end of the tension bar is fixedly connected to the fixed member, while a fixed end thereof abuts against an inner wall of the model box; two support chutes are formed on the inner wall of the model box in a vertical direction, the insertion strips are inserted into the support chutes and move in the vertical direction; the weight storage device and the landslide device are fixed on the angle control panel successively from the top down; the load balancing device is disposed on the top of the landslide model; one end of the water outlet pipe is communicated with the control box water outlet, while the other end thereof is extended into the model box to be suspended over the landslide model; the remote control devices are arranged on the telescoping control sensors, at the control box water outlet, at the control box water inlet, on the weight storage devices and on the tension bar, respectively; and, the remote control device arranged at the control box water inlet is communicatively connected to the water sensor probes and the anti-overflow device.

The landslide experimental device further includes a reservoir, a water inlet pipe, a drainage tank and a drainage pipe; the reservoir is fixedly mounted on a side of the top of the model box adjacent to the near-constant water flow control box; a reservoir water outlet and a water injection port are formed on the reservoir; one end of the water inlet pipe is communicated with the reservoir water outlet, while the other end thereof is communicated with the control box water inlet; the drainage tank is fixed on a side face of the model box and disposed below the near-constant water flow control box; a drainage tank water inlet is formed on the drainage tank, and a drainage port is formed on the model box; and, one end of the drainage pipe is communicated with the drainage tank water inlet, while the other end thereof is communicated with the drainage port.

The load balancing device further includes a stressed plate, an elastic stressed strip and a load basket; one end of the elastic stressed strip is connected to the bottom of the load basket, while the other end thereof is connected to the top of the stressed plate; and, the stressed plate is disposed on the top of the landslide model.

Several compartments each having an opening are provided within the weight storage device; triangular open plates are provided on two sides of the opening on the weight storage device; and, a baffle for occluding the opening is hinged between one sides of two adjacent open plates.

The landslide experimental device further includes a fixed bar; the fixed bar is fixed on the inner wall of the model box, two telescoping control sensors are mounted on the bottom of the fixed bar, and a remote control device is mounted at the drainage port.

The landslide experimental device further includes a centrifuge and a mobile terminal, with the mobile terminal being communicatively connected to each remote control device, and the model box being fixed on the centrifuge.

The present invention further provides a landslide experimental method for simulating a constant seepage flow, including the following steps:

step 1: a reservoir, a near-constant water flow control box and a drainage tank are fixed on a model box at a suitable height; an angle control panel and a tension bar are then connected together by a fixed member, and finally the tension bar is fixed on an inner bottom of the model box; and insertion strips of the angle control panel are inserted into support chutes of an inner wall of the model box, and the difference in height between two telescoping control sensors is controlled by adjusting a telescopic device according to the precision required by an experiment;

step 2: a weight storage device and a load balancing device are provided on the angle control panel, and a landslide model is prepared according to specific requirements of the experiment; the amount of water required by the experiment is injected into the reservoir, ball weights of different weights are placed within compartments of the weight storage device by weight, respectively, and finally the whole model box is fixed on a centrifuge;

step 3: the centrifuge test is activated, and when the centrifuge gravity achieves the experimental requirement, on the exterior of the centrifuge, a remote control device is controlled to open a control box water outlet by a mobile terminal; under the control of the remote control device, the water level in the near-constant water flow control box is always between the height differences of two telescoping control sensors, in this case, a near-constant water flow flows into the top of a landslide device through a water outlet pipe; and when a seepage flow flows out of the bottom of the landslide device, it flows through a drainage port, and finally flows into the drainage tank through a drainage pipe;

step 4: when external force load effects are considered simultaneously, the remote control device is controlled by the mobile terminal, and then baffles of different compartments are controlled to open and close, and thus ball weights of different weights enter into the load balancing device from the weight storage device;

step 5: when the angle of a landslide needs to be changed in the experiment, the remote control device is controlled by the mobile terminal to control the length of a tension bar, so that a tension end of the tension bar is extended or shortened to change the angle of the landslide; and step 6: when the influence of the water level on the landslide needs to be considered in the experiment, the remote control device is controlled by the mobile terminal to close a drainage tank water inlet; under the control of the remote control device, the water level in the model box can be between height differences of two telescoping control sensors and stabilized at a water level; and when the water level is raised or lowered, two telescoping control sensors are controlled to raise or lower simultaneously, and thus the impact of the water level on the landslide is controlled.

In the step 3, the water flow of the reservoir enters into the near-constant water flow control box, and when the water level in the box reaches the lower water sensor probe, the lower water sensor probe sends a signal to the remote control device immediately, and the remote control device controls the control box water inlet to open; when the water level continues to raise to reach the higher water sensor probe, the higher water sensor probe sends a signal to the remote control device immediately, and the remote control device controls the control box water inlet to close; in this case, the water level is lowered, and when the water level is lowered to the lower water sensor probe, the lower water sensor probe sends a signal to the remote control device immediately, and the remote control device controls the control box water inlet to open.

In the step 3, when the water level in the near-constant water flow control box is raised to an anti-overflow device, the anti-overflow device immediately sends a signal to the remote control device which controls the control box water inlet to be permanently closed and the control box water inlet needs to be reset before it can be opened again.

In the step 6, when the influence of the water level on the landslide needs to be considered in the experiment, the remote control device is controlled by the mobile terminal to close the drainage tank water inlet; when the water level in the model box continues to rise to the higher water sensor probe, the remote control device controls drainage tank water inlet to open. Under the control of the remote control device, the water level in the model box can be between the height differences of two telescoping control sensors and stabilized at a water level; and when the water level is raised or lowered, two telescoping control sensors are controlled to raise or lower simultaneously, and thus the impact of the water level below the landslide on the landslide is controlled.

Beneficial effects of the present invention are as follows.

In the present invention, with the landslide experiment of simulating a constant seepage flow and weight load by the remote control device, the constant seepage water flow can be realized by controlling the opening and closing of the water inlet of the control box through the remote control device to keep the water level the in water flow control box between the height differences of two telescoping control sensors. A near-constant seepage flow can be completely achieved, which is more conformable to the case where there may be seepage in the actual landslides more, so that the experiment is more accurate and the precision of the experimental result is improved.

The remote control device is arranged on the tension bar, and then the landslide device adjusts the gradient by the tension bar. The influences on the model landslide stability at different landslide angles under the condition of the seepage flow and weight load can be simulated, so that the requirements of exploring the landslide stability in multiple operating modes are achieved. On the other hand, by controlling the drainage port, the impact of the water level on the landslide can be investigated.

In the present invention, the structure is simple, both the assembly and disassembly are simple, time-saving and labor saving, and the operation is simple and easy to understand. Not only the time for mounting and replacing experimental apparatuses can be reduced, but also the disadvantage that the near-constant seepage flow cannot be manually operated under super gravity is eliminated.

REFERENCE NUMERALS

1—model box; 2—near-constant water flow control box; 3—load balancing device; 4—weight storage device; 5—angle control panel; 6—tension bar; 7—reservoir; 8—drainage tank; 9—remote control device; 10—water inlet pipe; 11—water outlet pipe; 12—drainage pipe; 13—water permeable plate; 14—support chute; 15—drainage port; 16—landslide model; 17—fixed bar; 21—control box water outlet; 22—control box water inlet; 23—anti-overflow device; 24—telescoping control sensor; 25—water sensor probe; 26—telescopic device; 31—stressed plate; 32—elastic stressed strip; 33—load basket; 41—compartment; 42—opening; 43—open plate; 44—baffle; 51—insertion strip; 52—fixed member; 61—tension end; 62—fixed end; 71—reservoir water outlet; 72—water injection port; 81—drainage tank water inlet.

DETAILED DESCRIPTION OF THE INVENTION

The present invention will be further described below in detail by specific embodiments with reference to the accompanying drawings.

Figure 1:
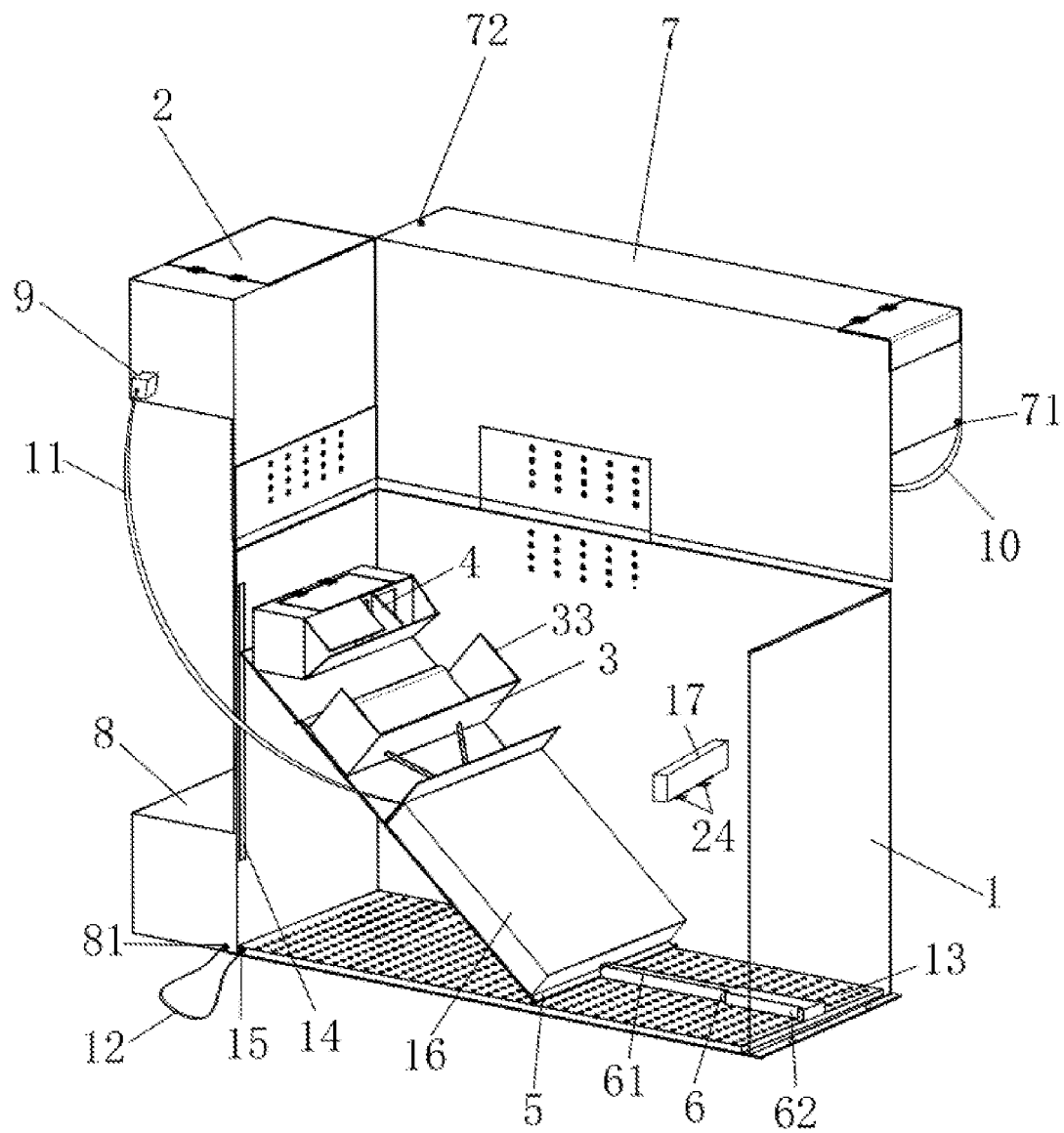
FIG. 1 is a semi-sectional view of the structure of the present invention.
Figure 2:
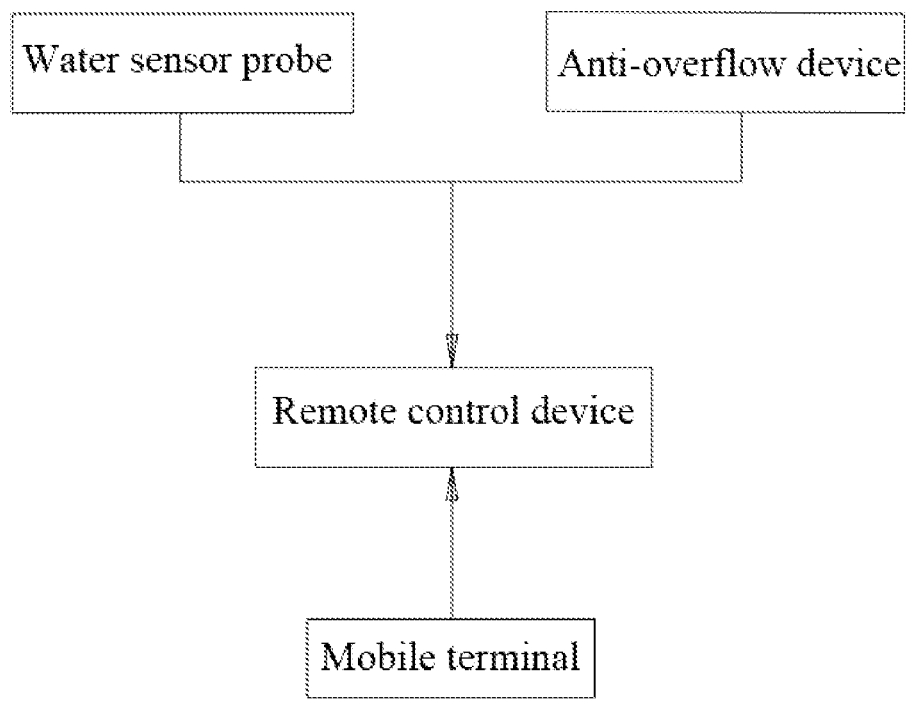
FIG. 2 is a circuit connection diagram of the present invention.
Figure 3:
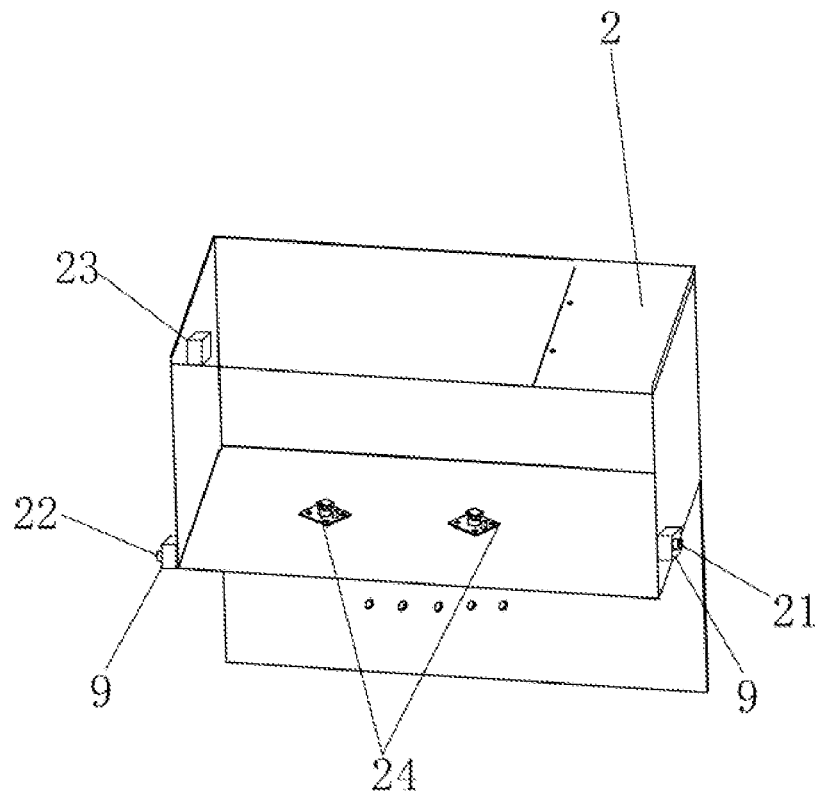
FIG. 3 is a semi-sectional view of the structure of a near-constant water flow control box.
Figure 4:
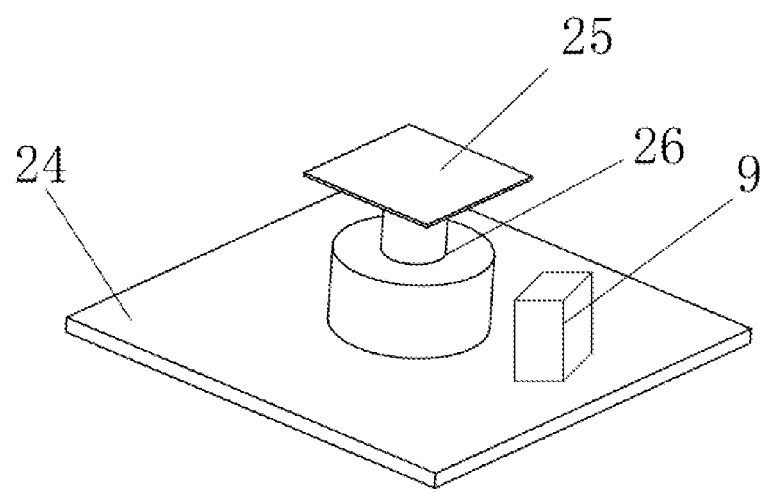
FIG. 4 is a schematic structural diagram of a telescoping control sensor.
Figure 5:
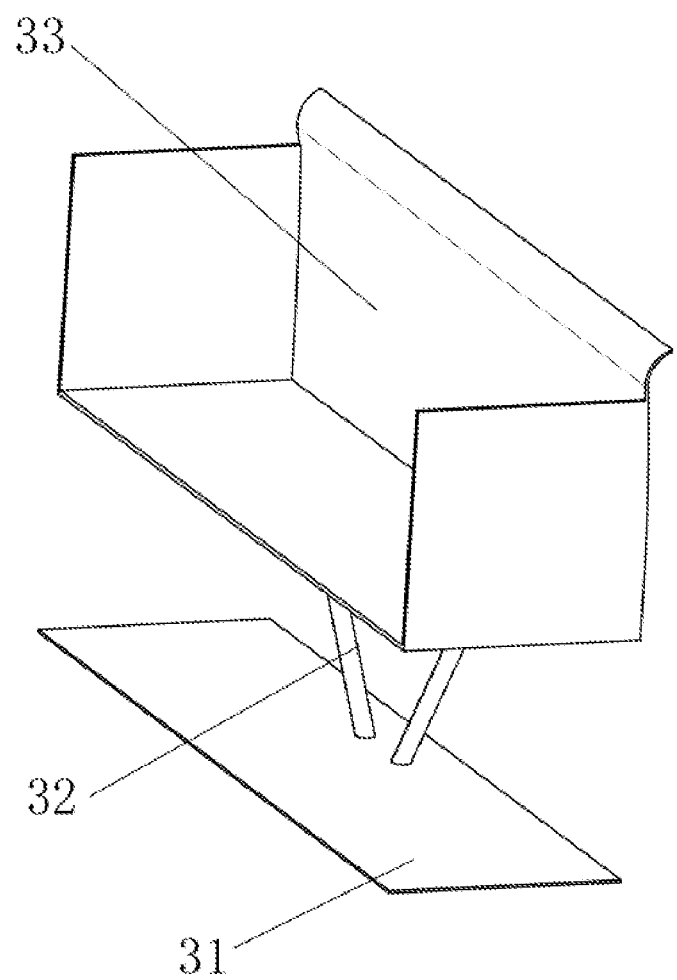
FIG. 5 is a schematic structural diagram of a load balancing device.
Figure 6:
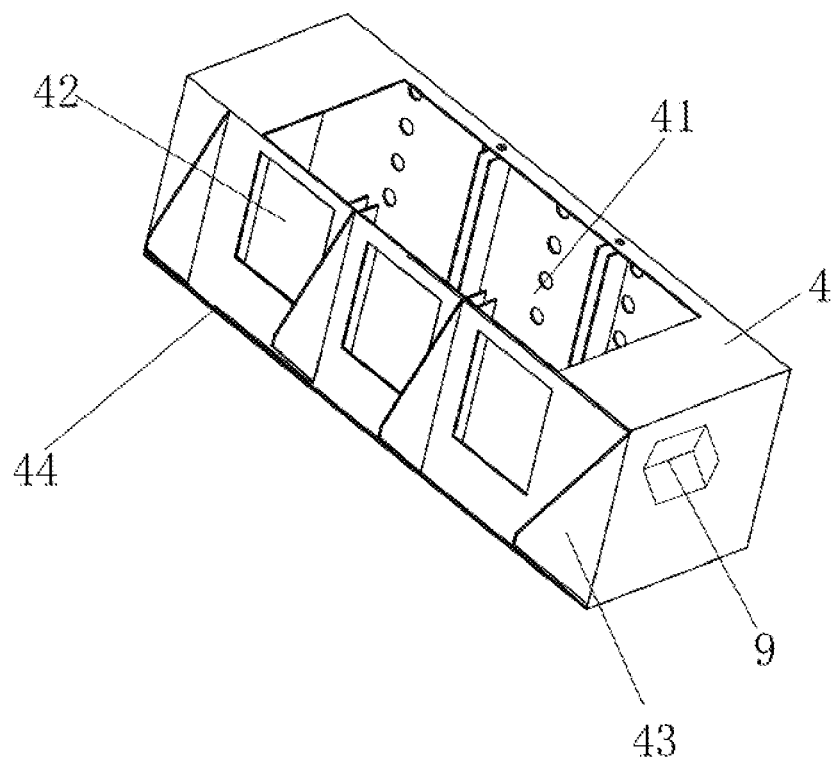
FIG. 6 is a schematic structural diagram of a weight storage device.
Figure 7:
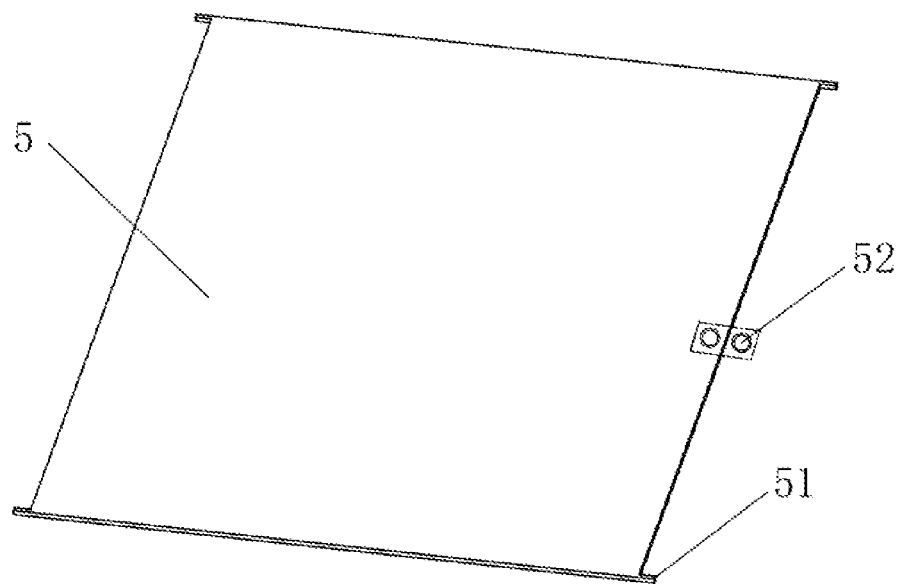
FIG. 7 is a schematic structural diagram of an angle control panel.

Referring to FIGS. 1 to 6, the present invention relates to a landslide experimental device for simulating a constant seepage flow, comprising a model box 1, a landslide device, a near-constant water flow control box 2, a water outlet pipe 11 and several remote control devices 9; the landslide device is mounted within the model box 1, the near-constant water flow control box 2 is fixedly mounted on the top of the model box 1, and a control box water outlet 21 and a control box water inlet 22 are formed on the near-constant water flow control box 2; an anti-overflow device 23 is disposed at an upper end of an inner wall of the near-constant water flow control box 2, and two telescoping control sensors 24 are mounted on an inner bottom of the near-constant water flow control box 2; each of the telescoping control sensors 24 includes a water sensor probe 25 and a telescopic device 26 which can lengthen and shorten; the landslide device includes a landslide model 16, a load balancing device 3, a weight storage device 4, an angle control panel 5 and a tension bar 6; support chutes 14 are provided on two sides of the top of the angle control panel 5, and a fixed member 52 is provided on the bottom of the angle control panel 5; a tension end 61 of the tension bar 6 is fixedly connected to the fixed member 52, while a fixed end 62 thereof abuts against an inner wall of the model box 1; two support chutes 14 are formed on the inner wall of the model box 1 in a vertical direction, the insertion strips 51 are inserted into the support chutes 14 and move in the vertical direction; the weight storage device 4 is fixed on the angle control panel 5; the load balancing device 3 is disposed on the top of the landslide model 16; one end of the water outlet pipe 11 is communicated with the control box water outlet 21, while the other end thereof is extended into the model box 1 to be suspended over the landslide model 16; the remote control devices 9 are arranged on the telescoping control sensors 24, at the control box water outlet 21, at the control box water inlet 22, on the weight storage devices 4 and on the tension bar 6, respectively; and, the remote control device 9 arranged at the control box water inlet 22 is communicatively connected to the water sensor probes 25 and the anti-overflow device 23.

In the present invention, with the landslide experiment of simulating a constant seepage flow and weight load by the remote control device 9, the constant seepage water flow can be realized by controlling the opening and closing of the water inlet 22 of the control box through the remote control device 9 to keep the water level between height differences of two telescoping control sensors 24. A near-constant seepage flow can be completely achieved, which is more conformable to the case where there may be seepage in the actual landslides more, so that the experiment is more accurate and the precision of the experimental result is improved. The remote control device 9 is arranged on the tension bar 6, and then the landslide device adjusts the gradient by the tension bar 6. The influences on the model landslide stability at different landslide angles under the condition of the seepage flow and weight load can be simulated, so that the requirements of exploring the landslide stability in multiple operating modes are achieved. In the present invention, the structure is simple, both the assembly and disassembly are simple, time-saving and labor-saving, and the operation is simple and easy to understand. Not only the time for mounting and replacing experimental apparatuses can be reduced, but also the disadvantage that the near-constant seepage flow cannot be manually operated under super gravity is eliminated.

In this embodiment, the landslide experimental device further includes a reservoir 7, a water inlet pipe 10, a drainage tank 8 and a drainage pipe 12; the reservoir 7 is fixedly mounted on a side of the top of the model box 1 adjacent to the near-constant water flow control box 2; a reservoir water outlet 71 and a water injection port 72 are formed on the reservoir 7; one end of the water inlet pipe 10 is communicated with the reservoir water outlet 71, while the other end thereof is communicated with the control box water inlet 22; the drainage tank 8 is fixed on a side face of the model box 1 and disposed below the near-constant water flow control box 2; a drainage tank water inlet 81 is formed on the drainage tank 8, and a drainage port 15 is formed on the model box 1; and, one end of the drainage pipe 12 is communicated with the drainage tank water inlet 81, while the other end thereof is communicated with the drainage port 15.

With the solution described above, the reservoir 7 injects the water flow into the near-constant water flow control box 2 through the water inlet pipe 10, and then the constant state of the water flow in the near-constant water flow control box 2 can be maintained, which is more conformable to the case where there may be seepage in the actual landslides more, so that the experiment is more accurate and the precision of the experimental result is improved; and by communicating the model box 1 with the drainage tank 8 by the drainage pipe 12, the influences on the landslide after the seepage flow flows down in the experiment can be solved.

In this embodiment, the load balancing device 3 includes a stressed plate 31, an elastic stressed strip 32 and a load basket 33; one end of the elastic stressed strip is connected to the bottom of the load basket 33, while the other end thereof is connected to the top of the stressed plate 31; and, the stressed plate 31 is disposed on the top of the landslide model 16. Several compartments 41 each having an opening 42 are provided within the weight storage device 4; triangular open plates 43 are provided on two sides of the opening 42 on the weight storage device 4; and, a baffle 44 for occluding the opening 42 is hinged between one sides of two adjacent open plates 43.

With the solution described above, the load balancing device 3 and the weight storage device 4 are arranged, compartments 41 where ball weights of different weights can be placed are arranged within the weight storage device 4, and the baffle 44 is hinged on the front of the opening 42 of the compartment 41; the baffle 44 is controlled to open and close by the remote control device 9, and then the influences of external forces on the model landslide stability are considered, so that the requirements of exploring the landslide stability in multiple operating modes are achieved.

In this embodiment, the landslide experimental device further comprises a fixed bar 17; the fixed bar 17 is fixed on the inner wall of the model box 1, two telescoping control sensors 24 are mounted on the bottom of the fixed bar 17, and a remote control device 9 is mounted at the drainage port 15.

With the solution described above, the fixed bar 17 is fixedly arranged at the water level of the model box 1, so that the water level in the model box is always between height differences of two telescoping control sensors 24, and thus the impact of the water level below the landslide on the landslide can be detected by two telescoping control sensors 24; a remote control device 9 is mounted at the drainage port 15, and the control of the water level in the model box 1 can be achieved by controlling the remote control device 9.

In this embodiment, the landslide experimental device further includes a centrifuge and a mobile terminal, with the mobile terminal being communicatively connected to each remote control device 9, and the model box 1 being fixed on the centrifuge.

With the solution described above, the gravity is simulated with the centrifugal force provided by the centrifuge, and the stress state of the model box 1 in the centrifugal force field is identical with the prototype in the gravity field according to the similarity criterion, so that the experiment is more accurate and the precision of the experimental result is improved. Through the communicative connection of the mobile terminal to each remote control device 9, remote control of the whole experiment can be achieved.

As a preferred implementation of the present invention, the landslide experimental device further includes a water permeable plate 13; the water permeable plate 13 is placed within the model box 1, the landslide device is mounted on the water permeable plate 13, and when the seepage flow flows out of the bottom of the landslide device, soil samples are filtered through the water permeable plate 13, and finally the seepage flow flows into the drainage tank 8 through the drainage pipe 12.

The present invention will be further described below by specific implementations.

The present invention further relates to a landslide experimental method for simulating a constant seepage flow, including the following steps:

step 1: a reservoir 7, a near-constant water flow control box 2 and a drainage tank 8 are fixed on a model box 1 at a suitable height; an angle control panel 5 and a tension bar 6 are then connected together by a fixed member 52, and finally the tension bar 6 is fixed on an inner bottom of the model box 1; and insertion strips 51 of the angle control panel 5 are inserted into support chutes 14 of an inner wall of the model box 1, and the difference in height between two telescoping control sensors 24 is controlled by adjusting a telescopic device 26 according to the precision required by an experiment;

step 2: a weight storage device 4 and a load balancing device 3 are provided on the angle control panel, and the amount of water required by the experiment is injected into the reservoir 7; ball weights of different weights are placed within compartments 41 of the weight storage device 4 by weight, respectively, and finally the whole model box 1 is fixed on a centrifuge;

step 3: the centrifuge test is activated, and when the centrifuge gravity achieves the experimental requirement, on the exterior of the centrifuge, a remote control device 9 is controlled to open a control box water outlet 21 by a mobile terminal; under the control of the remote control device 9, the water level in the near-constant water flow control box 2 is always between height differences of two telescoping control sensors 24, in this case, a near-constant water flow flows into the top of a landslide device through a water outlet pipe 11; and when a seepage flow flows out of the bottom of the landslide device, it flows through a drainage port 15, and finally flows into the drainage tank 8 through a drainage pipe 12;

step 4: when external force load effects are considered simultaneously, the remote control device 9 is controlled by the mobile terminal, and then baffles 44 of different compartments 41 are controlled to open and close, and thus ball weights of different weights enter into the load balancing device 3 from the weight storage device 4 and the process of loading by external forces is simulated, and the influences of external forces on the model landslide stability are further considered;

step 5: when the angle of a landslide needs to be changed in the experiment, the remote control device 9 is controlled by the mobile terminal to control the length of a tension bar 6, so that a tension end 61 of the tension bar 6 is extended or shortened to change the angle of the landslide; and step 6: when the influence of the water level on the landslide needs to be considered in the experiment, the remote control device 9 is controlled by the mobile terminal to close the drainage tank water inlet 81; under the control of the remote control device 9, the water level in the model box 1 can be between height differences of two telescoping control sensors 24 and stabilized at a water level; and when the water level is raised or lowered, two telescoping control sensors 24 are controlled to raise or lower simultaneously, and thus the impact of the water level on the landslide is controlled.

In the step 3, the water flow of the reservoir 7 enters into the near-constant water flow control box 2, and when the water level in the box reaches the lower water sensor probe 25, the lower water sensor probe 25 sends a signal to the remote control device 9 immediately, and the remote control device 9 controls the control box water inlet 22 to open; when the water level continues to raise to reach the higher water sensor probe, the higher water sensor probe 25 sends a signal to the remote control device 9 immediately, and the remote control device 9 controls the control box water inlet 22 to close; in this case, the water level is lowered, and when the water level is lowered to the lower water sensor probe 25, the lower water sensor probe 25 sends a signal to the remote control device 9 immediately, and the remote control device 9 controls the control box water inlet 22 to reopen; and the state is cycled in this way to achieve the condition of the near-constant water flow is reached. When the water level is raised to an anti-overflow device 23, the anti-overflow device 23 sends a signal to the remote control device 9 immediately, and the remote control device 9 controls the control box water inlet 22 to be permanently closed and the control box water inlet 22 needs to be reset before it can be opened again. When two telescoping control sensors 24 are controlled to raise or lower simultaneously, the water level is raised or lowered simultaneously, so that the impact of the water level on the landslide model can be studied.

When the experiment is finished, soil samples of the landslide model inside the model box 1 are cleaned, and components are disassembled.

The implementations are merely preferred implementations of the present invention and not intended to limit the scope of the present invention. Various transformations and improvements made to the technical solutions of the present invention by a person of ordinary skill in the art without departing from the design spirit of the present invention shall fall into the protection scope defined by the claims of the present invention.

What is claimed is:

1. A landslide experimental device for simulating a constant seepage flow, comprising a model box and a landslide device mounted within the model box, characterized in that the landslide experimental device further comprises a near-constant water flow control box, a water outlet pipe and several remote control devices;

wherein the near-constant water flow control box is fixedly mounted on a top of the model box, and a control box water outlet and a control box water inlet are formed on the near-constant water flow control box; an anti-overflow device is disposed at an upper end of an inner wall of the near-constant water flow control box, and two telescoping control sensors are mounted on an inner bottom of the near-constant water flow control box; each of the telescoping control sensors comprises a water sensor probe and a telescopic device which can lengthen and shorten;

wherein the landslide device comprises a landslide model, a load balancing device, a weight storage device, an angle control panel and a tension bar; insertion strips are provided on two sides of a top of the angle control panel, and a fixed member is provided on a bottom of the angle control panel; a tension end of the tension bar is fixedly connected to the fixed member, while a fixed end thereof abuts against an inner wall of the model box; two support chutes are formed on the inner wall of the model box in a vertical direction, the insertion strips are inserted into the support chutes and move in the vertical direction; the weight storage device is fixed on the angle control panel; the load balancing device is disposed on the top of the landslide model;

wherein one end of the water outlet pipe is communicated with the control box water outlet, while the other end thereof is extended into the model box to be suspended over the landslide model;

wherein the remote control devices are arranged on the telescoping control sensors, at the control box water outlet, at the control box water inlet, on the weight storage devices and on the tension bar, respectively; and, the remote control device arranged at the control box water inlet is communicatively connected to the water sensor probes and the anti-overflow device.

2. The landslide experimental device for simulating a constant seepage flow according to claim 1, further comprising a reservoir, a water inlet pipe, a drainage tank and a drainage pipe;

wherein the reservoir is fixedly mounted on a side of the top of the model box adjacent to the near-constant water flow control box; a reservoir water outlet and a water injection port are formed on the reservoir;

wherein one end of the water inlet pipe is communicated with the reservoir water outlet, while the other end thereof is communicated with the control box water inlet;

wherein the drainage tank is fixed on a side face of the model box and disposed below the near-constant water flow control box; a drainage tank water inlet is formed on the drainage tank, and a drainage port is formed on the model box;

and wherein, one end of the drainage pipe is communicated with the drainage tank water inlet, while the other end thereof is communicated with the drainage port.

3. The landslide experimental device for simulating a constant seepage flow according to claim 2, further comprising a fixed bar; the fixed bar is fixed on an inner wall of the model box, two telescoping control sensors are mounted on a bottom of the fixed bar, and a remote control device is mounted at the drainage port.

4. The landslide experimental device for simulating a constant seepage flow according to claim 1, characterized in that the load balancing device comprises a stressed plate, an elastic stressed strip and a load basket; one end of the elastic stressed strip is connected to a bottom of the load basket, while the other end thereof is connected to a top of the stressed plate; and, the stressed plate is disposed on a top of the landslide model.

5. The landslide experimental device for simulating a constant seepage flow according to claim 1, characterized in that several compartments each having an opening are provided within the weight storage device; triangular open plates are provided on two sides of the opening on the weight storage device; and, a baffle for occluding the opening is hinged between one sides of two adjacent open plates.

6. The landslide experimental device for simulating a constant seepage flow according to claim 1, further comprising a centrifuge and a mobile terminal, with the mobile terminal being communicatively connected to each remote control device, and the model box being fixed on a centrifuge machine.

* * * * *